(12) United States Patent
Park (10) Patent No.: US 11,517,470 B2
(45) Date of Patent: Dec. 6, 2022

(54) LIP SEALING TAPE

(71) Applicant: Mi Ra Park, Seoul (KR)

(72) Inventor: Mi Ra Park, Seoul (KR)

( * ) Notice: Subject to any disclaimer, the term of this patent is extended or adjusted under 35 U.S.C. 154(b) by 394 days.

(21) Appl. No.: 16/764,165

(22) PCT Filed: Nov. 12, 2018

(86) PCT No.: PCT/KR2018/013711
§ 371 (c)(1),
(2) Date: May 14, 2020

(87) PCT Pub. No.: WO2019/098621
PCT Pub. Date: May 23, 2019

(65) Prior Publication Data
US 2020/0390593 A1 Dec. 17, 2020

(30) Foreign Application Priority Data
Nov. 20, 2017 (KR) ........................ 10-2017-0154558

(51) Int. Cl.
*A61F 5/56* (2006.01)
*B33Y 10/00* (2015.01)
*B33Y 50/02* (2015.01)
*C09J 7/30* (2018.01)

(52) U.S. Cl.
CPC .............. *A61F 5/56* (2013.01); *B33Y 10/00* (2014.12); *B33Y 50/02* (2014.12); *C09J 7/30* (2018.01); *Y10S 602/902* (2013.01)

(58) Field of Classification Search
CPC .......... A61F 5/56; A61F 13/02; A61F 13/122; B33Y 10/00; B33Y 50/02; B33Y 80/00; C09J 7/30; C09J 2301/10; C09J 7/20; Y10S 602/902
See application file for complete search history.

(56) References Cited

U.S. PATENT DOCUMENTS

| | | | | |
|---|---|---|---|---|
| 2011/0265802 A1* | 11/2011 | Ha | ............................ | A61F 5/56 |
| | | | | 128/848 |
| 2014/0000632 A1* | 1/2014 | Chen | ........................ | A61F 5/56 |
| | | | | 128/848 |
| 2014/0366889 A1* | 12/2014 | Riley | ........................ | A61F 9/04 |
| | | | | 128/845 |

FOREIGN PATENT DOCUMENTS

| | | |
|---|---|---|
| JP | 10-305100 A | 11/1998 |
| JP | 11-076286 A | 3/1999 |
| JP | 3160894 U * | 7/2010 |
| JP | 03160894 U | 7/2010 |

(Continued)

*Primary Examiner* — Tarla R Patel
(74) *Attorney, Agent, or Firm* — Novick, Kim & Lee PLLC; Jae Youn Kim (57) ABSTRACT

A lip sealing tape for preventing a user's mouth from opening in daily life and during sleep is proposed. The lip sealing tape adds a mouth-closing vector to assist a vector that displaces a position of a user's tongue forward and upward, thereby forming a closed vector system of muscles of the entire body to increase physical stability and induce nasal respiration (breathing through a user's nose) to gradually reduce oral respiration while promoting nasal respiration. The lip sealing tape is characterized by simply adding the mouth-closing vector to prevent opening of the user's upper and lower lips, by means of horizontal and vertical adhesive tape portions, thereby minimizing a contact area with a user's facial skin when worn and thus minimizing discomfort due to stuffiness while maximizing safety when worn.

7 Claims, 8 Drawing Sheets

(56) References Cited

FOREIGN PATENT DOCUMENTS

| JP | 03193679 U | 10/2014 |
|---|---|---|
| JP | 2017-038657 A | 2/2017 |
| KR | 20-0405903 Y1 | 1/2006 |
| KR | 10-0912498 B1 | 8/2009 |
| KR | 20-2011-0006260 U | 6/2011 |
| KR | 10-1636436 B1 | 7/2016 |
| KR | 10-2016-0109454 A | 9/2016 |
| KR | 10-1874951 B1 | 7/2018 |

* cited by examiner

FIG. 6 forward rotation of mandible, change in shape of back wall of upper airway, change in angle of cervical spine, distance increase between first cervical vertebrae and occipital bone

FIG. 7 forward rotation of mandible, change in shape of back wall of upper airway, change in angle of cervical spine, distance increase between first cervical vertebrae and occipital bone

LIP SEALING TAPE

TECHNICAL FIELD

The present invention relates generally to a lip sealing tape that adds a mouth-closing vector to assist a vector that displaces the position of a user's tongue forward and upward, thereby forming a closed vector system of muscles of the entire body to increase physical stability and induce nasal respiration and healthy sleep. More particularly, the present invention relates to a lip sealing tape that assists a mouth-closing vector in preventing opening of a user's upper and lower lips except when a user's mouth is intentionally opened, thereby assisting a user's tongue in forward-upward lifting to allow the tongue to stay in full contact with a user's palate, so that a superficial front line (pulmonary muscles including the lips) and a deep front line (suprahyoid muscles including the tongue, infrahyoid muscles, and muscles for connection thereof) are closed and thus a neutral zone of muscles involved in teeth arrangement is placed closer to an original position. This allows a user's teeth to be brought into a more correct arrangement, secures efficient nasal respiration, and obtains a more correct skeletal correction with less force during long-term use, thereby enabling the user to maintain a correct posture with respect to gravity. Further, promoted nasal respiration helps in relieving intranasal diseases (rhinitis, atopy) and enables sufficient oxygen supply to the body. This helps in keeping respiration stable during sleep and thus improving health and quality of life (QOL).

BACKGROUND ART

Anatomically, muscles of a human body have to form a closed vector system so that a resultant force with respect to gravity is zero and the sum of rotational moments is zero at any moment when lying, sitting, standing, walking, or running to achieve stability. However, as people who have an open vector system that does not achieve such stability are increasing day by day, they may experience chronic pain in a part of the body, body asymmetry such as malocclusion, asymmetry of temporomandibular joints, and facial asymmetry, which are accompanied by rhinitis, strabismus, torticollis, and spinal disc disease. As a solution to fix these symptoms, splints, orthodontics, chiropractic, chuna manual therapy, pain treatment, skeletal correction treatment, double-jaw surgery, nasal septum removal surgery, posture correction devices, and the like are used. In these treatments, however, it is necessary to consider the vector sum of muscles forming a closed vector system of the entire body.

To form the closed vector system, among all the muscles of the body, muscles that can be opened during functioning have to be closed during non-functioning. For example, in medicine, for the case where the anus or urethra are open, there is a disease named fecal incontinence or urinary incontinence, but there is no disease name for the case where the tongue does not touch the palate and the lips are apart. However, there are only disease names such as facial asymmetry, malocclusion, strabismus, and torticollis caused thereby. Therefore, there is a need for a way to form a closed vector system as a more fundamental solution.

When a person breathes, the air has to pass through soft tissues such as the nasal cavity (nose, hereinafter referred to as "nasal cavity"), tonsils, airway, and the like. At this time, the tongue has to stay in contact with the palate. During the daytime, the surrounding muscles help the tissues stay in place in the conscious state, maintaining a sufficient air passage, but during sleep, the muscles are relaxed and stretched in the unconscious state, which partially narrows the airway, i.e., the air passage, and as the air flows into the narrowed passage, the surrounding soft tissues vibrate, causing snoring.

This snoring phenomenon occurs by severe muscle relaxation during sleep, or when the air passage is completely blocked due to other causes such as drugs or obesity and the air is briefly prevented from entering the lungs at all. This is called sleep apnea, and in this case, it is impossible to get good sleep due to arousal of the brain.

It is reported that if this condition continues periodically, the lungs do not get oxygen in the air, so the risk of death from stroke or heart attack during sleep is about 2 to 3 times higher among those who suffer from sleep apnea than normal people.

It is reported that snoring not only interferes with comfortable sleep, but also leads to serious diseases such as myocardial infarction, heart attack, and stroke, and people's interest in snoring treatment is increasing.

As of now, many types of products to prevent or reduce snoring have been developed, from pajamas with air back plates to prevent a person from sleeping on his/her back to snoring warning pillows. While these instruments and devices are somewhat effective in temporary reduction of snoring, there is a disadvantage in that sleep and correct muscle positioning are disturbed. Additionally, respiratory aids (CPAP, BIPAP) that can treat sleep apnea have been developed and used in developed countries. These devices act as air splints for airway obstruction due to negative pressure when inhaling by injecting air of a constant positive pressure in accordance with breathing through an oxygen mask in the form of a gas mask. However, there are disadvantages in that the devices are very costly, a mask has to be worn to cover the entire face, which may cause side effects such as anxiety and nasal dryness and obstruction, and it is inconvenient to carry the devices. On the other hand, in order to induce nasal respiration while preventing oral respiration, methods such as surgery and treatment with drugs, attaching a porous tape that covers the mouth while allowing passage of air, tying a strap to secure the chin to the head, inserting an implant into the nose or mouth, and the like are used. However, these methods cause skin irritation or irritate the head or temporomandibular joints, causing insomnia, are impossible use for a long term due to side effects such as drug addiction, and are difficult to popularize due to economic burden and wearing discomfort. On the other hand, in order to prevent snoring, a mask has been proposed to force a wearer to breathe by supplying air from an air tank attached to his/her back. This method, however, only allows the wearer to sleep on his/her side because of the air tank attached to his/her back, which puts pressure on the heart or organs. Additionally, since sleeping on the wearer's back is not allowed, those who usually sleep on their back cannot go into deep sleep, causing unilateral shoulder deformity and limited movement.

Thus, in an effort to the above-mentioned problems, an application for a 'mask for preventing mouth opening during sleep' has been filed. This mask, however, causes stuffiness and discomfort when worn, and is difficult to wear in summer due to sweat. Additionally, this mask is configured to cover the entire face and thus is high in manufacturing cost, and is inconvenient to use due to the feeling of stuffiness.

In an effort to solve the above-mentioned problems, the following related art documents have been applied, but there still remains a problem in that not all of the above-mentioned problems of the related art can be solved.

DOCUMENTS OF RELATED ART (Patent Document 1) Korean Patent No. 10-0912498 (2009. Aug. 10)
(Patent Document 2) Korean Patent No. 10-1636436 (2016. Jun. 29)
(Patent Document 3) Korean Patent Application Publication No. 10-2016-0109454 (2016. Sep. 21)
(Patent Document 4) Korean Utility Model Registration No. 20-0405903 (2006. Jan. 4)
(Patent Document 5) Korean Utility Model Application Publication No. 20-2011-0006260 (2011. Jun. 22)

DISCLOSURE

Technical Problem

Accordingly, the present invention has been made keeping in mind the above problems occurring in the related art, and a first objective of the present invention is to provide a lip sealing tape, including a connection adhesive tape portion, a philtrum adhesive tape portion, and a pogonion adhesive tape portion, and a menton adhesive tape portion. A second objective of the present invention is to provide a lip sealing tape, wherein opening of a user's mouth is prevented during sleep, and nasal respiration (breathing through a user's nose) is induced to gradually reduce oral respiration while promoting nasal respiration, and nasal hygiene is promoted. A third objective of the present invention is to provide a lip sealing tape, wherein the lip sealing tape is worn during sleep to open a user's airway by pulling a user's mandible forward and upward and thus securing an air passage. A fourth objective of the present invention is to provide a lip sealing tape, wherein the lip sealing tape serves to close a conception vessel, which is one of meridians in oriental medicine, so that closing the conception vessel contributes to increasing qi circulation throughout a user's body, and communication between the conception vessel and a governor vessel is promoted, which contributes to promoting qi circulation throughout the user's body. A fifth objective of the present invention is to provide a lip sealing tape, wherein a fluid passage from a user's nostrils and a user's alveoli is formed due to the influence of nasal respiration induced by the lip sealing tape, thereby forming a positive pressure by fluid in accordance with Bernoulli's law to form a vector that lifts a user's head and a user's thoracic cavity in the opposite direction of gravity. A sixth objective of the present invention is to provide a lip sealing tape, wherein a vertical adhesive tape portion is connected from a user's philtrum to a user's hyoid bone with a user's upper and lower lips slightly rolled inward and closes a superficial front line in the running direction of muscle to give a vector to also close a deep front line, thereby forming a closed vector system of muscles of the entire body so that the vector sum is zero to increase physical stability. A seventh objective of the present invention is to provide a lip sealing tape, wherein the vertical adhesive tape portion connected from the user's philtrum to the user's hyoid bone makes vectors of the superficial front line and the deep front line into closed curves to promote communication of the conception vessel in qi circulation in oriental medicine, thereby promoting communication between the conception vessel and the governor vessel. An eighth objective of the present invention is to provide a lip sealing tape, wherein a horizontal adhesive tape portion stabilize the vertical adhesive tape portion by attachment to a position above the user's upper lip, to pogonion, and to menton, and the position and number of the horizontal adhesive tape portion are changed as the magnitude of a patient's mouth-closing vector increases. A ninth objective of the present invention is to provide a lip sealing tape, wherein when the lip sealing tape is worn on the user during sleep, nasal respiration is induced while suppressing oral respiration, without stuffiness or discomfort to the user, thereby reducing disorders such as dry mouth, snoring, and sleep apnea, and assisting in strengthening oral muscles involved in mouth closing. A tenth objective of the present invention is to provide a lip sealing tape, wherein the lip sealing tape is worn on a user's facial skin with a minimum contact area with the skin, thereby minimizing discomfort, maximizing safety, and effectively performing a function of preventing mouth opening while reducing manufacturing cost. An eleventh objective of the present invention is to provide a lip sealing tape, wherein respective members constituting the lip sealing tape are coupled to each other by a fastening means, and the distances between the members are easily controlled, so that anyone can easily attach and detach the lip sealing tape to fit his/her facial anatomy. A twelfth objective of the present invention is to provide a lip sealing tape, wherein the lip sealing tape is attached around the user's lips and firmly holds the user's upper and lower lips in a closed position to prevent opening of the lips during sleep, thereby inducing nasal respiration that relieves symptoms such as snoring, dry mouth, and sleep apnea that may occur during sleep. A thirteenth objective of the present invention is to provide a lip sealing tape, wherein the surface area where the lip sealing tape is attached from the philtrum to the menton is about $\frac{1}{6}$ to $\frac{1}{5}$ of the lateral width of the lips, so that the lip sealing tape is attached around the user's lips and firmly holds the user's upper and lower lips in a closed position to prevent opening of the lips during sleep, while allowing the user to cough out secretions or vomit occurring when a reaction such as nausea or vomiting occurs during wearing, thereby preventing airway obstruction. A fourteenth objective of the present invention is to provide a lip sealing tape, wherein the lip sealing tape is attached around the user's lips and firmly holds the user's upper and lower lips in a closed position to prevent opening of the lips during sleep, while allowing the user to speak when wearing the lip sealing tape due to elasticity thereof. A fifteenth objective of the present invention is to provide a lip sealing tape, wherein the lip sealing tape is attached around the user's lips and firmly holds the user's upper and lower lips in a closed position to prevent opening of the lips during sleep, while generating an action, such as hydroplaning of a glass plate, on the user's upper and lower lips by means of saliva in the user's mouth, thereby enabling natural closing of the mouth. A sixteenth objective of the present invention is to provide a lip sealing tape, wherein the lip sealing tape is attached around the user's lips and firmly holds the user's upper and lower lips in a closed position to prevent opening of the lips during sleep, thereby inducing nasal respiration so that positive pressure acts on a user's upper airway, thereby allowing inflammatory substances present in a user's sinuses to be naturally discharged to the user's nostrils or the user's mouth. A seventeenth objective of the present invention is to provide a lip sealing tape, wherein the lip sealing tape is attached around the user's lips and firmly holds the user's upper and lower lips in a closed position to prevent opening of the lips during sleep, thereby inducing nasal respiration so that nitric oxide synthase of nasal and sinus mucosa is activated to increase immunity by sterilizing action, and smooth muscle relaxation and cardiovascular muscle relaxation is induced (the subject of the 1998 Nobel Prize in Physiology or Medicine). A eighteenth objective of the present invention is to provide a lip sealing tape, wherein the lip sealing tape is attached around the user's lips and firmly holds the user's upper and lower lips in a closed position to prevent opening of the lips during sleep, thereby inducing nasal respiration, and allowing lugdunin, which is an antibiotic present in the nasal and sinus mucosa, to act to eradicate superbacteria, thereby increasing immunity (Nature 2016). A nineteenth objective of the present invention is to provide a lip sealing tape, wherein the lip sealing tape is attached around the user's lips and firmly holds the user's upper and lower lips in a closed position to prevent opening of the lips during sleep, thereby increasing the magnitude of a vector that allows a user's tongue to touch a user's palate, thereby forming a closed vector system of muscles of the entire body to increase physical stability.

Technical Solution

In order to accomplish the above objectives, the present invention provides a lip sealing tape for preventing a user's mouth from opening in daily life and during sleep, the lip sealing tape adding a mouth-closing vector to assist a vector that displaces a position of a user's tongue forward and upward, thereby forming a closed vector system of muscles of the entire body to increase physical stability and induce nasal respiration (breathing through a user's nose) to gradually reduce oral respiration while promoting nasal respiration, wherein the lip sealing tape may simply add the mouth-closing vector to prevent opening of the user's upper and lower lips, by means of horizontal and vertical adhesive tape portions, thereby minimizing a contact area with a user's facial skin when worn and thus minimizing discomfort due to stuffiness while maximizing safety when worn, and reducing manufacturing cost with a simple structure.

Advantageous Effects

As described in detail above, a lip sealing tape according to the present invention for inducing healthy sleep includes a connection adhesive tape portion, a philtrum adhesive tape portion, and a pogonion adhesive tape portion, and a menton adhesive tape portion.

In the present invention having the above-described technical configuration, opening of a user's mouth is prevented during sleep, and nasal respiration (breathing through a user's nose) is induced to gradually reduce oral respiration while promoting nasal respiration, and nasal hygiene is promoted.

Further, in the present invention, the lip sealing tape is worn during sleep to open a user's airway by pulling a user's mandible forward and upward and thus securing an air passage.

Further, in the present invention, the lip sealing tape serves to close a conception vessel, which is one of meridians in oriental medicine, so that closing the conception vessel contributes to increasing qi circulation throughout a user's body, and communication between the conception vessel and a governor vessel is promoted, which contributes to promoting qi circulation throughout the user's body.

Further, in the present invention, a fluid passage from a user's nostrils and a user's alveoli is formed due to the influence of nasal respiration induced by the lip sealing tape, thereby forming a positive pressure by fluid in accordance with Bernoulli's law to form a vector that lifts a user's head and a user's thoracic cavity in the opposite direction of gravity.

Further, in the present invention, a vertical adhesive tape portion is connected from a user's philtrum to a user's hyoid bone with a user's upper and lower lips slightly rolled inward and closes a superficial front line in the running direction of muscle to give a vector to also close a deep front line, thereby forming a closed vector system of muscles of the entire body so that the vector sum is zero to increase physical stability.

Further, in the present invention, the vertical adhesive tape portion connected from the user's philtrum to the user's hyoid bone makes vectors of the superficial front line and the deep front line into closed curves to promote communication of the conception vessel in qi circulation in oriental medicine, thereby promoting communication between the conception vessel and the governor vessel.

In particular, in the present invention, a horizontal adhesive tape portion stabilize the vertical adhesive tape portion by attachment to a position above the user's upper lip, to pogonion, and to menton, and the position and number of the horizontal adhesive tape portion are changed as the magnitude of a patient's mouth-closing vector increases.

Further, in the present invention, when the lip sealing tape is worn on the user during sleep, nasal respiration is induced while suppressing oral respiration, without stuffiness or discomfort to the user, thereby reducing disorders such as dry mouth, snoring, and sleep apnea, and assisting in strengthening oral muscles involved in mouth closing.

Further, in the present invention, the lip sealing tape is worn on a user's facial skin with a minimum contact area with the skin, thereby minimizing discomfort, maximizing safety, and effectively performing a function of preventing mouth opening while reducing manufacturing cost.

Further, in the present invention, respective members constituting the lip sealing tape are coupled to each other by a fastening means, and the distances between the members are easily controlled, so that anyone can easily attach and detach the lip sealing tape to fit his/her facial anatomy.

Further, in the present invention, the lip sealing tape is attached around the user's lips and firmly holds the user's upper and lower lips in a closed position to prevent opening of the lips during sleep, thereby inducing nasal respiration that relieves symptoms such as snoring, dry mouth, and sleep apnea that may occur during sleep.

Further, in the present invention, the surface area where the lip sealing tape is attached from the philtrum to the menton is about ⅙ to ⅓ of the lateral width of the lips, so that the lip sealing tape is attached around the user's lips and firmly holds the user's upper and lower lips in a closed position to prevent opening of the lips during sleep, while allowing the user to cough out secretions or vomit occurring when a reaction such as nausea or vomiting occurs during wearing, thereby preventing airway obstruction.

Further, in the present invention, the lip sealing tape is attached around the user's lips and firmly holds the user's upper and lower lips in a closed position to prevent opening of the lips during sleep, while allowing the user to speak when wearing the lip sealing tape due to elasticity thereof. Further, in the present invention, the lip sealing tape is attached around the user's lips and firmly holds the user's upper and lower lips in a closed position to prevent opening of the lips during sleep, while generating an action, such as hydroplaning of a glass plate, on the user's upper and lower lips by means of saliva in the user's mouth, thereby enabling natural closing of the mouth.

Further, in the present invention, the lip sealing tape is attached around the user's lips and firmly holds the user's upper and lower lips in a closed position to prevent opening of the lips during sleep, thereby inducing nasal respiration so that positive pressure acts on a user's upper airway, thereby allowing inflammatory substances present in a user's sinuses to be naturally discharged to the user's nostrils or the user's mouth.

Further, in the present invention, the lip sealing tape is attached around the user's lips and firmly holds the user's upper and lower lips in a closed position to prevent opening of the lips during sleep, thereby inducing nasal respiration so that nitric oxide synthase of nasal and sinus mucosa is activated to increase immunity by sterilizing action, and smooth muscle relaxation and cardiovascular muscle relaxation is induced (the subject of the 1998 Nobel Prize in Physiology or Medicine).

Further, in the present invention, the lip sealing tape is attached around the user's lips and firmly holds the user's upper and lower lips in a closed position to prevent opening of the lips during sleep, thereby inducing nasal respiration, and allowing lugdunin, which is an antibiotic present in the nasal and sinus mucosa, to act to eradicate superbacteria, thereby increasing immunity (Nature 2016).

Lastly, in the present invention, the lip sealing tape is attached around the user's lips and firmly holds the user's upper and lower lips in a closed position to prevent opening of the lips during sleep, thereby increasing the magnitude of a vector that allows a user's tongue to touch a user's palate, thereby forming a closed vector system of muscles of the entire body to increase physical stability.

Hereinafter, exemplary embodiments of the present invention for achieving these effects will be described in detail with reference to the accompanying drawings.

DESCRIPTION OF THE REFERENCE NUMERALS IN THE DRAWINGS

100: lip sealing tape
110: connection adhesive tape portion
120: philtrum adhesive tape portion
130: pogonion adhesive tape portion
140: menton adhesive tape portion

BEST MODE

A lip sealing tape according to the present invention is configured as illustrated in FIGS. 1 to 9.

In the following description of the present invention, detailed descriptions of known functions and components incorporated herein will be omitted when it may make the subject matter of the present invention unclear.

Further, technical terms, as will be mentioned hereinafter, are terms defined in consideration of their function in the present invention, which may be varied according to the intention of a user, practice, or the like, so that the terms should be defined based on the contents of this specification.

In the drawings, the size or and thickness of each component is expressed arbitrarily for clarity of illustration, but due to this, the protective scope of the present invention should not be interpreted narrowly.

First, the present invention provides a lip sealing tape 100 for preventing a user's mouth from opening in daily life and during sleep, the lip sealing tape 100 inducing nasal respiration (breathing through a user's nose, hereinafter referred to as 'nasal respiration') to reduce oral respiration while promoting respiration. The lip sealing tape 100 characterized by simply adding a mouth-closing vector to prevent opening of a user's upper and lower lips, by means of horizontal and vertical adhesive tape portions, thereby minimizing the contact area with a user's facial skin when worn and thus minimizing discomfort due to stuffiness and maximizing safety when worn, while reducing manufacturing cost with a simple structure.

In particular, the lip sealing tape 100 according to the present invention is configured as follows.

That is, at least one connection adhesive tape portion 110 vertically or diagonally attached to a position passing over a user's upper and lower lips is provided.

Further, a philtrum adhesive tape portion 120 located at an upper end of the connection adhesive tape portion 110 and horizontally attached to a position between a user's nose and the user's upper lip is provided.

Further, a pogonion adhesive tape portion 130 located at a lower end of the connection adhesive tape portion 110 and horizontally attached on a horizontal line between a position below the point (B) and pogonion (Pog) is provided.

Lastly, a menton adhesive tape portion 140 located at a lower end of the connection adhesive tape portion 110 horizontally attached on a horizontal line between the gnathion (Gn) and menton (Me) is provided.

Here, a multi-use adhesive surface 150 adhered to a user's skin to be fixed and having proven skin safety is provided on a back surface of each of the respective adhesive tape portions.

The adhesive surface 150 is made of a material that has proven skin safety and can be used repeatedly, so that in the case of severe oral respiration or excessive mandibular displacement, adhesive force is limited to a degree that does not cause skin damage.

Further, a release film 160 being removably in contact with the adhesive surface 150 and protecting the adhesive surface 150 is provided.

Further, the connection adhesive tape portion 110, the philtrum adhesive tape portion 120, the pogonion adhesive tape portion 130, and the menton adhesive tape portion 140 are provided integrally as a single body, or are provided separately.

Further, it is preferable that the philtrum adhesive tape portion 120 and the connection adhesive tape portion 110 are formed in a "T" shape that integrally connects a horizontal line directly below a user's philtrum, and a vertical line from the philtrum to a position below a curvature point on a user's mandible.

Further, it is preferable that the horizontal philtrum adhesive tape portion 120, pogonion adhesive tape portion 130, and menton adhesive tape portion 140 are attached to the vertical connection adhesive tape portion 110 at right angles to maintain accurate adhesive force.

Further, it is preferable that the lip sealing tape 100 according to the present invention is custom-manufactured to fit a user's facial anatomy by 3D scanning and printing.

The present invention may be variously modified and may have various forms in applying the above-described components.

It should be understood that the present invention is not limited to the particular forms mentioned in the detailed description above, but rather includes all modifications, equivalents, and substitutes within the spirit and scope of the invention as defined by the appended claims.

Operational effects of the lip sealing tape according to the present invention configured as described above will be described as follows.

First, the present invention is characterized by simply adding a mouth-closing vector to prevent opening of the user's upper and lower, thereby assisting in moving a user's tongue forward and upward and thus forming a closed vector system of muscles of the entire body in daily life and during sleep, thereby increasing physical stability and promoting nasal respiration while promoting nasal hygiene.

Figure 1:
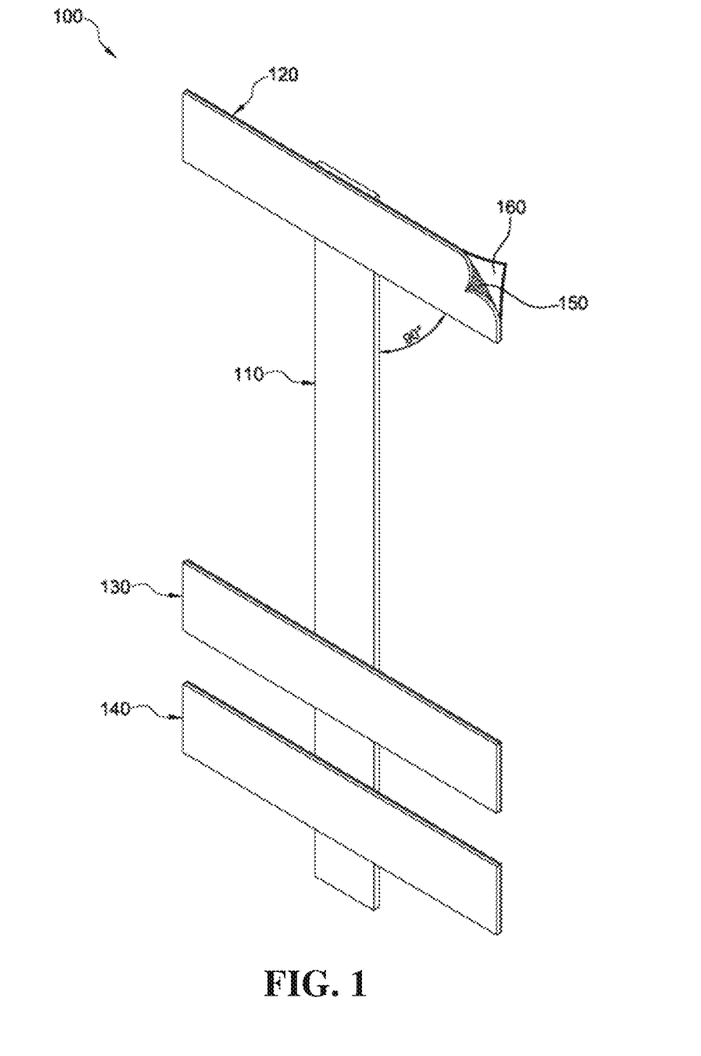
FIG. 1 is a perspective view illustrating a lip sealing tape according to the present invention.

To this end, FIG. 1 illustrates a perspective view illustrating the lip sealing tape 100 according to the present invention.

Figure 2:
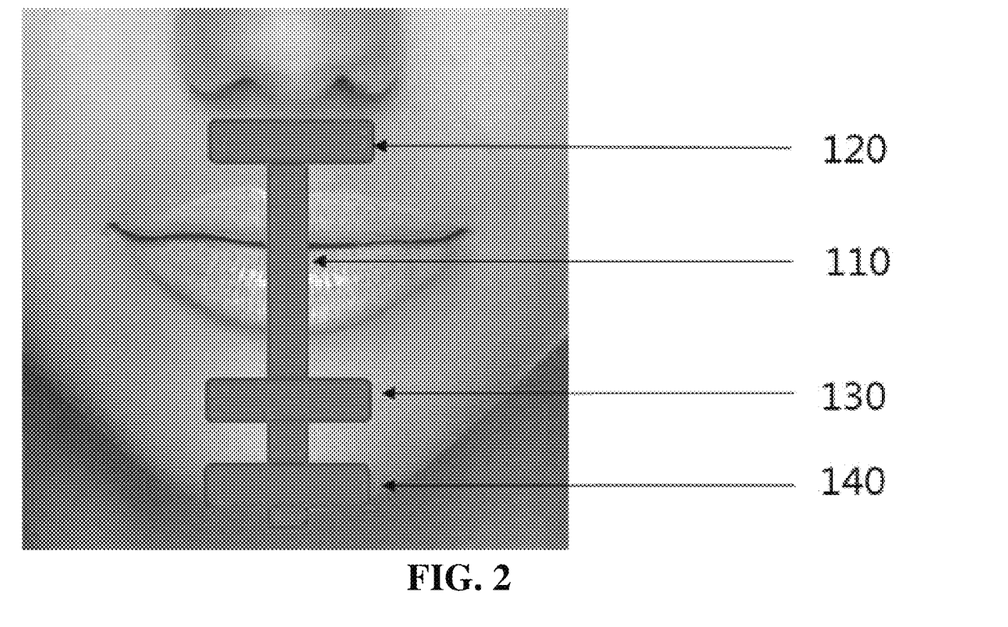
FIG. 2 is an exemplary view illustrating a use state of the lip sealing tape according to the present invention.

FIG. 2 illustrates a front exemplary view illustrating a use state of the lip sealing tape 100 according to the present invention.

In order to use the lip sealing tape 100 according to the present invention, first, the release film 160 provided on the back surface of each of the adhesive tape portions is removed.

Then, the philtrum adhesive tape portion 120 and the connection adhesive tape portion 110 are attached to positions above the user's upper lip and below the user's lower lip.

That is, in the present invention, a "T"-shaped tape that integrally connects the horizontal line right below the user's philtrum, and the vertical line from the philtrum to the position below the curvature point on the user's mandible is attached. Here, the adhesive surface 150 provided on the back surface of each of the adhesive tape portions is adhered to the user's skin to be fixed, and is made of a material having proven skin safety.

Then, the pogonion adhesive tape portion 130 that is horizontally attached on the horizontal line between the position below the point (B) (see FIG. 4) below and the pogonion (Pog) (see FIG. 4) is attached to the lower end of the connection adhesive tape portion 110.

Subsequently, the menton adhesive tape portion 140 that is horizontally attached on the horizontal line between the gnathion (Gn) (see FIG. 4) and the menton (Me) (see FIG. 4) is attached to the lower end of the connection adhesive tape portion 110.

Figure 3:
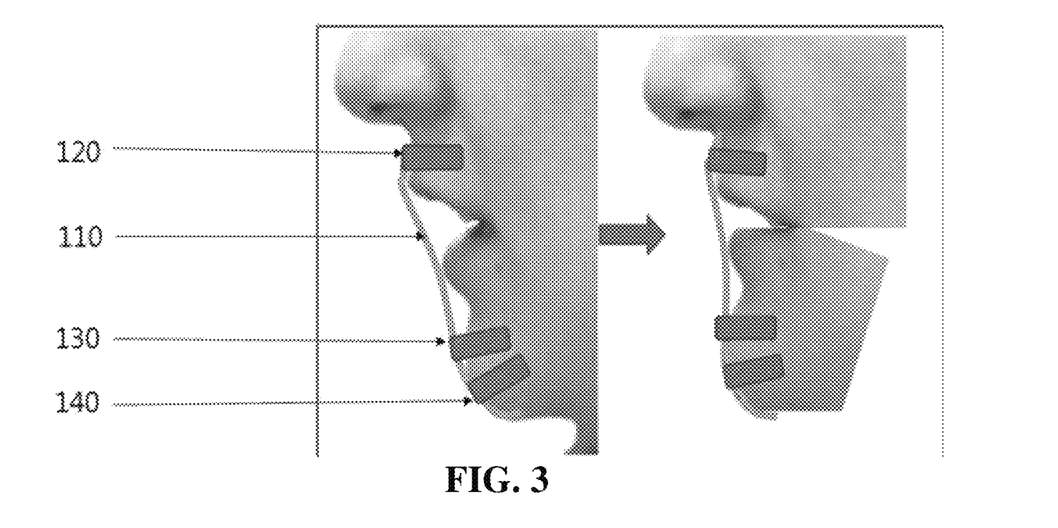
FIG. 3 is a comparison view illustrating a state before and after use of the lip sealing tape according to the present invention.
Figure 4:
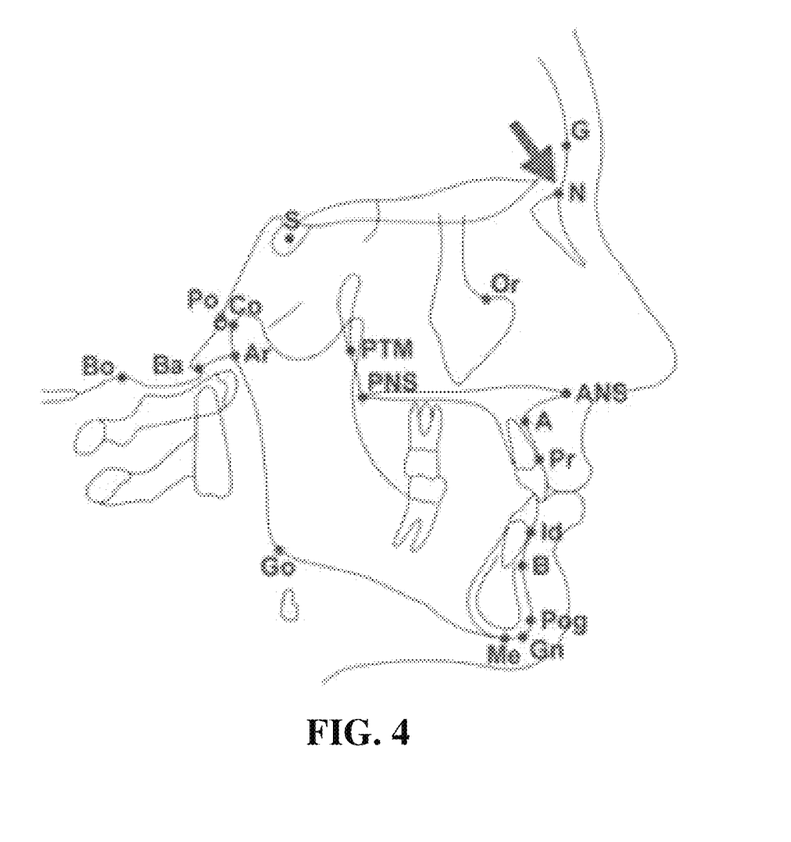
FIG. 4 is a view illustrating an anatomical structural of a human's head.

FIG. 3 illustrates a comparison view illustrating a state before and after use of the lip sealing tape 100 according to the present invention, from which it can be seen that a lot of changes have occurred compared to before use, as in the following X-ray photographs.

The lip sealing tape 100 according the present invention described above is vertically attached along a running line of a mouth-closing muscle to close a superficial front line so that the superficial front line becomes a closed curve and thus the vector sum of the surface front line is zero.

Further, in the present invention, the mouth-closing vector is added at the superficial front line to assist a vector that displaces the position of the user's tongue forward and upward, thereby forming a closed vector system of muscles of the entire body to form force equilibrium, thereby increasing physical stability, and changing a muscle vector forming a neutral zone in a physiological direction of each user over time.

Further, in the present invention, the lip sealing tape serves to close a conception vessel, which is one of meridians in oriental medicine, so that closing the conception vessel contributes to increasing qi circulation throughout a user's body. Further, communication between the conception vessel and a governor vessel is promoted, which contributes to promoting qi circulation throughout the user's body.

Further, in the present invention, a vertical adhesion range is limited to block a vector that pulls a tip of the user's nose downward, and block a vector that pulls the user's mandible downward backward by a large muscle such as sternocleidomastoid muscle located below a user's hyoid bone. Further, to increase positional stability of the connection adhesive tape portion 110, the horizontal line of the menton adhesive tape portion 140 has to be located above the menton so that the user's mandible can be pulled upward. When the horizontal line of the menton adhesive tape portion 140 is located below the menton, a vector that pulls the user's mandible downward is formed due to the influence of the sternocleidomastoid muscle (SCM) is formed.

On the other hand, in the present invention, the adhesive surface 150 made of a material that has proven skin safety and can be used repeatedly is used, so that in the case of severe oral respiration or excessive mandibular displacement, adhesive force is limited to the degree that does not cause skin damage thereby releasing adhesion. In this case, an initial adhesion time is short, but the adhesion time increases as the muscle vector forming the neutral zone is changed in the physiological direction.

Further, in the present invention, a fluid passage from a user's nostrils and a user's alveoli is formed due to the influence of nasal respiration induced by the lip sealing tape 100, thereby forming a positive pressure by fluid in accordance with Bernoulli's law to form a vector that lifts a user's head and a user's thoracic cavity in the opposite direction of gravity (the opposite direction of gravity when lying down, the opposite direction of gravity when standing, which is the direction perpendicular to the earth's surface).

Further, in the present invention, by inducing nasal respiration, oral respiration is gradually reduced.

The lip sealing tape 100 according to the present invention is custom-manufactured to fit a user's anatomy by 3D scanning and printing, thereby increasing mechanical stability of the lip sealing tape 100.

Further, in the present invention, a vertical tape is connected from the user's philtrum to the user's hyoid bone with the user's upper and lower lips slightly rolled inward and closes the superficial front line in the running direction of muscle to give a vector to also close a deep front line, thereby forming a closed vector system of muscles of the entire body so that the vector sum is zero to increase physical stability.

Further, in the present invention, the connection adhesive tape portion 110 (vertical adhesive tape portion) connected from the user's philtrum to the user's hyoid bone makes vectors of the superficial front line and the deep front line into closed curves to promote communication of the conception vessel in qi circulation in oriental medicine, thereby promoting communication between the conception vessel and the governor vessel.

Further, in the present invention, the pogonion adhesive tape portion 130 and the menton adhesive tape portion 140, which are horizontal adhesive tape portions, are attached to the pogonion and menton to stabilize the T-shaped tape. Further, the position and number of the horizontal adhesive tape portions are changed as the magnitude of a patient's mouth-closing vector increases.

As a result of the above effects, it can be seen that the condition of an actual patient is improved as follows.

Figure 5:
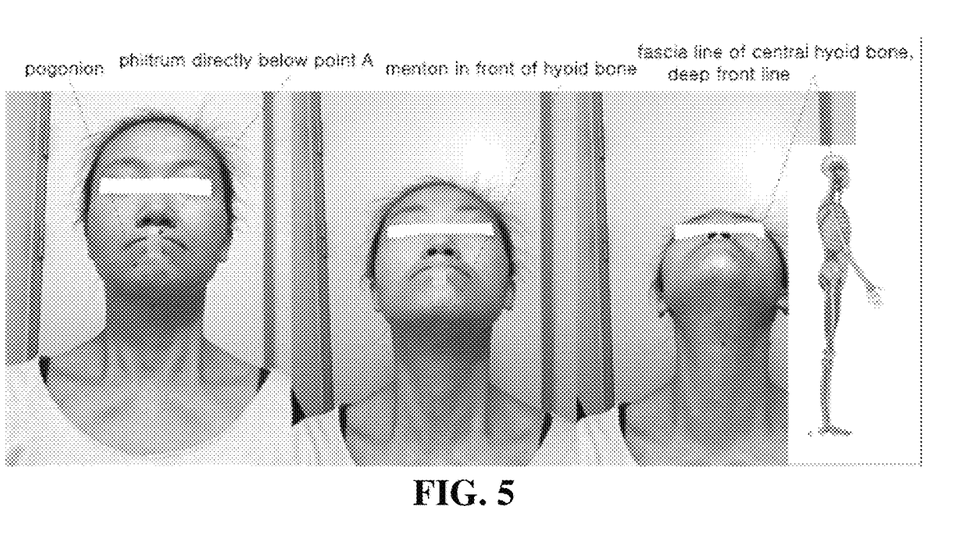
FIG. 5 is an explanatory view illustrating the use state of the lip sealing tape according to the present invention.

That is, FIG. 5 illustrates a view illustrating the use state of the lip sealing tape 100 according to the present invention, illustrating the pogonion, philtrum, menton in front of the hyoid bone, and fascia line of the central hyoid bone.

Figure 6:
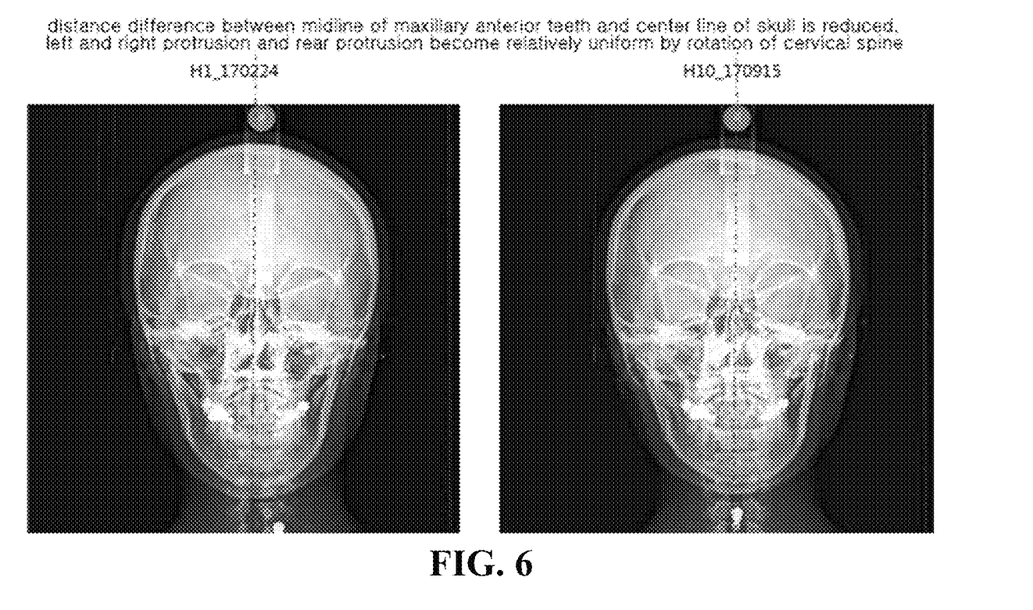
FIG. 6 is a view illustrating X-ray photographs (front view) before and after the use of the lip sealing tape according to the present invention.

FIG. 6 illustrates a view illustrating X-ray photographs (front view) before and after the use of the lip sealing tape 100 according to the present invention.

Figure 7:
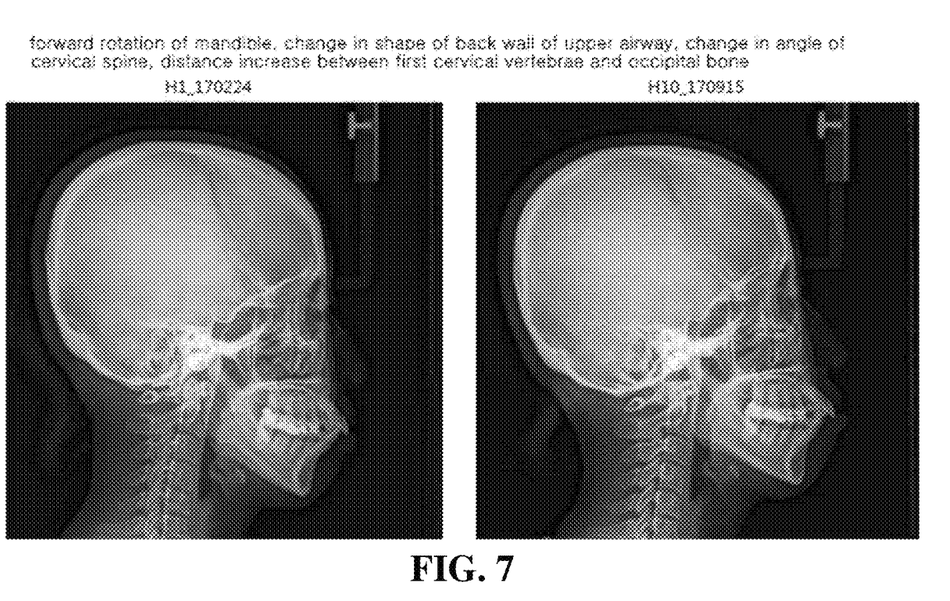
FIG. 7 is a view illustrating X-ray photographs (side view) before and after the use of the lip sealing tape according to the present invention.

FIG. 7 illustrates a view illustrating X-ray photographs (side view) before and after the use of the lip sealing tape 100 according to the present invention.

Figure 8:
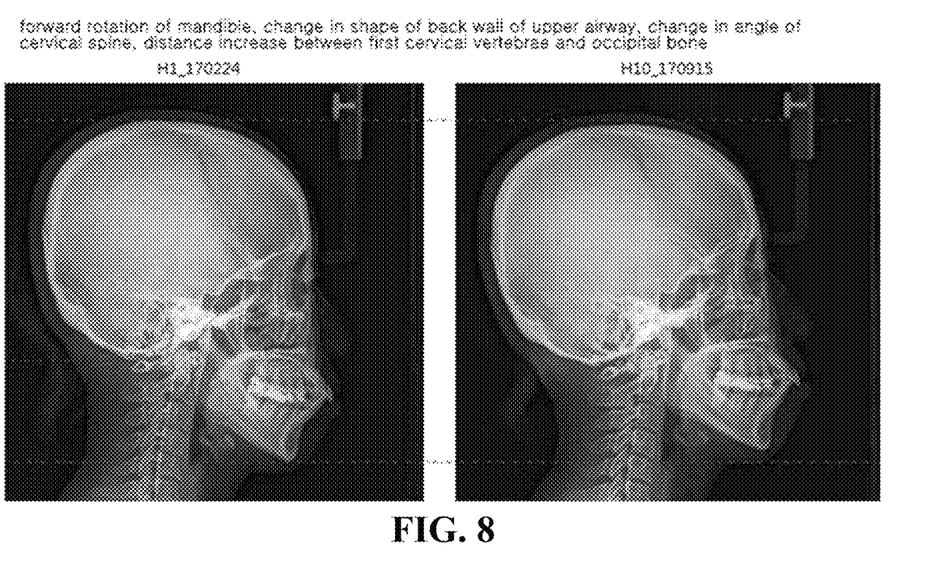
FIG. 8 is a view illustrating X-ray photographs (side view) before and after the use of the lip sealing tape according to the present invention, illustrating a distance increase.

FIG. 8 illustrates a view illustrating X-ray photographs (side view) before and after the use of the lip sealing tape 100 according to the present invention, illustrating a distance increase.

Figure 9:
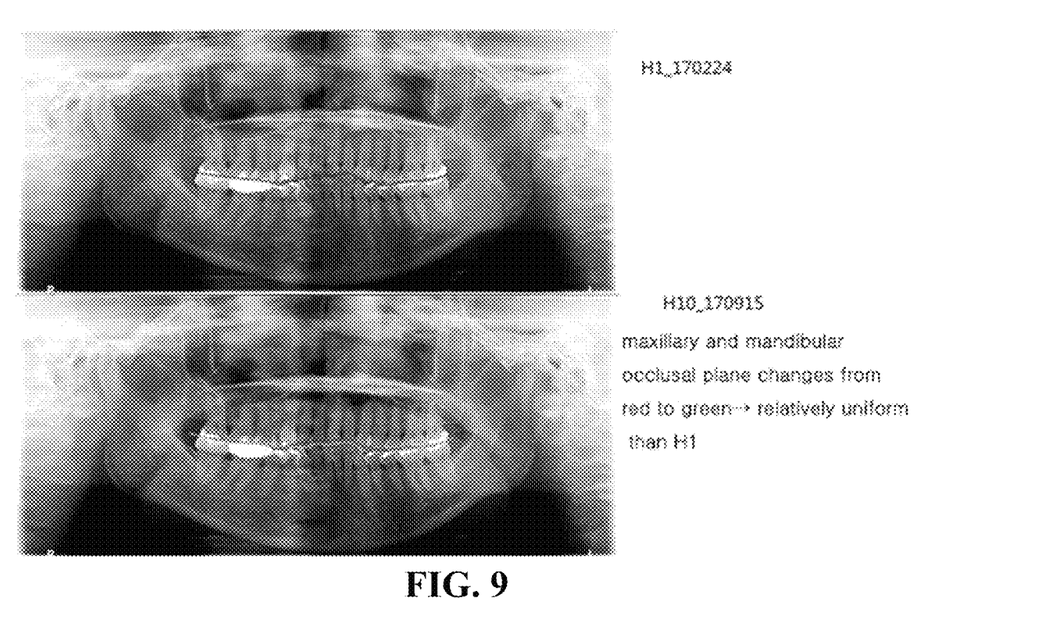
FIG. 9 is a view illustrating X-ray photographs illustrating a state of teeth before and after the use of the lip sealing tape according to the present invention.

FIG. 9 illustrates a view illustrating X-ray photographs illustrating a state of teeth before and after the use of the lip sealing tape 100 according to the present invention.

Therefore, the present invention obtains the above-described effects, and provides the effect that allows people of all age group to comfortably breathe only through their nose.

INDUSTRIAL APPLICABILITY

The technical idea of a lip sealing tape according to the present invention is that the same repeated results can be achieved in practice. In particular, the present invention can promote technological development, which contributes to industrial development, and thus the present invention is worth protecting.

The invention claimed is:

1. A lip sealing tape for preventing configured to prevent a user's mouth from opening in daily life and during sleep, the lip sealing tape adding a mouth-closing vector configured to assist a vector that displaces a position of a user's tongue forward and upward to form a closed vector system of muscles of a user's body to increase physical stability and induce nasal respiration, which is breathing through a user's nose, to gradually reduce oral respiration while promoting nasal respiration, wherein the lip sealing tape is configured to add the mouth-closing vector to prevent opening of a user's upper and lower lips, by horizontal and vertical adhesive tape portions, thereby minimizing a contact area with a user's facial skin when worn and thus minimizing discomfort due to stuffiness while maximizing safety when worn, and wherein the lip sealing tape comprises:

at least one connection adhesive tape portion configured to be vertically attached to a position passing over the user's upper and lower lips;

a philtrum adhesive tape portion located at an upper end of the connection adhesive tape portion, and configured to be horizontally attached to a position between a user's nose and the user's upper lip;

a pogonion adhesive tape portion located at a lower end of the connection adhesive tape portion, and configured to be horizontally attached on a horizontal line between a position below a point (B) and a user's pogonion (Pog); and a menton adhesive tape portion located beneath the pogonion adhesive tape portion and at the lower end of the connection adhesive tape portion, wherein the menton adhesive tape portion is configured to be horizontally attached on a horizontal line between a user's gnathion (Gn) and a user's menton (Me).

2. The lip sealing tape of claim 1, further comprising:

a multi-use adhesive surface provided on a back surface of each of the respective adhesive tape for attachment to a user's skin to be fixed, and having proven skin safety; and a release film being removably in contact with the adhesive surface and protecting the adhesive surface.

3. The lip sealing tape of claim 1, wherein the connection adhesive tape portion, the philtrum adhesive tape portion, the pogonion adhesive tape portion, and the menton adhesive tape portion are provided integrally as a single body, or are provided separately.

4. The lip sealing tape of claim 1, wherein the philtrum adhesive tape portion and the connection adhesive tape portion are formed in a "T" shape that is configured to integrally connect a horizontal line directly below a user's philtrum, and a vertical line from the philtrum to a position below a curvature point on a user's mandible.

5. The lip sealing tape of claim 1, wherein the horizontal philtrum adhesive tape portion, pogonion adhesive tape portion, and menton adhesive tape portion are attached to the vertical connection adhesive tape portion at right angles.

6. The lip sealing tape of claim 1, wherein the lip sealing tape is custom-manufactured to fit a user's facial anatomy by 3D scanning and printing.

7. The lip sealing tape of claim 1, wherein a surface area, where the lip sealing tape is configured to be attached from a user's philtrum to the user's menton, is about ⅙ to ⅕ of a lateral width of the user's upper and lower lips, so that the lip sealing tape is configured to be attached around the user's upper and lower lips and firmly hold the user's upper and lower lips in a closed position to prevent opening of the lips during sleep.

* * * * *